US008685072B2

(12) United States Patent
Neuberger

(10) Patent No.: US 8,685,072 B2
(45) Date of Patent: Apr. 1, 2014

(54) DEVICE AND METHOD FOR VESSEL TREATMENT

(75) Inventor: Wolfgang Neuberger, Dubai (AE)

(73) Assignee: Biolitec Pharma Marketing Ltd, Ft Labuan (MY)

( * ) Notice: Subject to any disclaimer, the term of this patent is extended or adjusted under 35 U.S.C. 154(b) by 0 days.

(21) Appl. No.: 12/877,721

(22) Filed: Sep. 8, 2010

(65) Prior Publication Data

US 2011/0060388 A1    Mar. 10, 2011

Related U.S. Application Data

(60) Provisional application No. 61/240,554, filed on Sep. 8, 2009.

(51) Int. Cl.
*A61N 5/06* (2006.01)
(52) U.S. Cl.
USPC .............................. 607/89; 607/88
(58) Field of Classification Search
USPC .................. 607/88–92; 606/15, 27
See application file for complete search history.

(56) References Cited

U.S. PATENT DOCUMENTS

| | | | | |
|---|---|---|---|---|
| 6,033,398 | A * | 3/2000 | Farley et al. | 606/27 |
| 6,398,777 | B1 * | 6/2002 | Navarro et al. | 606/7 |
| 6,981,972 | B1 * | 1/2006 | Farley et al. | 606/27 |
| 2003/0191512 | A1 * | 10/2003 | Laufer et al. | 607/101 |
| 2004/0078032 | A1 * | 4/2004 | Frenz et al. | 606/15 |
| 2005/0015123 | A1 * | 1/2005 | Paithankar | 607/88 |
| 2006/0069417 | A1 * | 3/2006 | Farley et al. | 607/101 |
| 2006/0189967 | A1 * | 8/2006 | Masotti et al. | 606/15 |
| 2010/0100162 | A1 * | 4/2010 | Peyman | 607/102 |
| 2011/0259343 | A1 * | 10/2011 | Karabey et al. | 128/831 |

* cited by examiner

*Primary Examiner* — Bill Thomson
*Assistant Examiner* — Jeffrey Lipitz
(74) *Attorney, Agent, or Firm* — Bolesh J. Skutnik; BJ Associates

(57) ABSTRACT

A device and method for restoring functionality of blood vessels are disclosed. Laser energy is accurately and precisely applied in order to restore vessel functionality. This is accomplished by a controlled, reliable and specific shrinkage and/or strengthening of the vessel structure by controlled transport of laser radiation via an optical fiber to the treatment site. Laser wavelength is chosen according to the required penetration depth in tissue. In a preferred embodiment, wavelength of approximately 1470 nm is used. A mini-endoscope is preferably used to control the process by visual inspection from the inside of the vessel but other means may also be combined to control the procedure. Full 360° radial emission, i.e., delivery of laser radiation perpendicularly or fairly inclined relative to the veins axis, is beneficial, and is accomplished by means of a radial emitting fiber. In another preferred embodiment, a 360 degree radiation pattern can be achieved by using a twister or side-emitting fiber, along with rotational and sweeping movements to apply energy in an even, more-controlled, and guided manner. Valve function is restored to recover whole vein functionality, avoiding the need of closing it. In a preferred embodiment, energy is applied from the outside of the vessel, by inserting a device through the skin and tissue. In another preferred embodiment, specific radiation absorbers are located at suitable positions inside the vessel wall, to selectively target radiation to tagged locations. Vessel function is restored preserving its structure. A wide range of vessel diameters are effectively treated. Vessels include veins, arteries and fistulas.

11 Claims, 2 Drawing Sheets

DEVICE AND METHOD FOR VESSEL TREATMENT

DOMESTIC PRIORITY UNDER 35 USC 119(e)

This application claims the benefit and priority of U.S. Provisional Application Ser. No. 61/240,554 filed Sep. 8, 2009, entitled "Device and Method for Vessel Treatment" by Wolfgang Neuberger, which is incorporated by reference herein.

BACKGROUND OF THE INVENTION

1. Field of the Invention

The present invention relates to minimally invasive treatments and in particular, to the treatment of vascular disorders by using local energy emitting devices and conveying means.

2. Invention Disclosure Statement

The blood vessels are the part of the circulatory system that transport blood throughout the body. There are three major types of blood vessels: the arteries, which carry the blood away from the heart, the capillaries, which enable the actual exchange of water and other substances between the blood and the tissues; and the veins, which carry blood from the capillaries back towards the heart.

Arteries and veins have the same basic structure. Three distinct layers can be identified, from inside to outside: tunica intima, tunica media and tunica adventitia. The main difference between arteries and veins is the proportions in which these components are present.

In the arterial system, blood pressure is usually around 120 mmHg systolic and 80 mmHg diastolic. In contrast, pressures in the venous system are constant and rarely exceed 10 mmHg.

The human venous system of the lower limbs consists essentially of the superficial venous system and the deep venous system, both connected by perforating veins. The superficial system comprises the great and the small saphenous veins, while the deep venous system includes the anterior and posterior tibial veins, which converge to form the popliteal vein near the knee. The popliteal vein, in turn, becomes the femoral vein when joined by the small saphenous vein.

The venous system comprises valves, whose main function is to achieve unidirectional blood flow back to the heart. Venous valves are usually bicuspid valves, with each cusp forming a blood reservoir, which force their free surfaces together under retrograde blood pressure. As a consequence, when properly operating, retrograde blood flow is prevented, allowing only antegrade flow to the heart. A valve becomes incompetent when their cusps are unable to seal properly under retrograde pressure gradient, so retrograde blood flow occurs. When retrograde blood flow occurs, pressure increases in the lower venous sections, dilating veins and usually leading to additional valvular failure.

Valvular failure, usually referred to as venous insufficiency, is a chronic disease that can lead to skin discoloration, varicose veins, pain, swelling and ulcerations. Varicose veins refer to blood vessels that have become enlarged and twisted and have progressively lost their wall elasticity. Due to the widening of the blood vessels, vein valves cannot be completely closed and veins lose their ability to carry blood back to the heart. This leads to an accumulation of blood inside the vessels, enlarging and twisting the veins even more. Furthermore, varicose veins usually have a blue or purple color and may protrude twisted above the surface of the skin, this being responsible for their characteristically unattractive appearance. They are commonly formed in the superficial veins of the legs, which are subject to high pressure when standing. Other types of varicose veins include venous lakes, reticular veins and telangiectasias. A special case of venous insufficiency may occur in arteriovenous fistulae: a connection between an artery and a vein. These can be congenital, surgically created or acquired due to pathologic process. A fistula may be surgically created for hemodialysis treatments (vascular access). Arteriovenous fistula for vascular access is carried out previous to hemodialysis treatment, in order to render a vein to grow larger and stronger for easy access to the blood system. As a consequence, an adequate vascular access is achieved, through which blood is withdrawn, purified, and returned to the body. Vascular accesses are thus entranceways into the bloodstream that lie completely beneath the skin. The access is usually in the arm, but sometimes in the leg, and can be performed by direct artery-vein anastomosis or by means of an artificial graft. Except for specific special cases artery-vein anastomosis are preferred, to eliminate risks associated with insertion of foreign bodies. It is well known that vascular accesses have a high incidence of complications, finally determining vascular access failure. These can be divided into non-thrombotic and thrombotic complications, finally determining vascular access failure. Regarding non-thrombotic complications, venous hypertension is one of the most important since it may cause valvular incompetence or central venous stenosis. This may lead to severe upper limb edema, skin discoloration, access dysfunction and peripheral ischemia with resultant fingertip ulceration.

There are a number of treatments available intending to cure these kinds of vascular pathologies. Some of them only consist in relief of symptoms but they do not treat varicose veins nor prevent them from forming. These include elevating the legs by lying down or using a footstool when sitting, elastic stockings and exercise.

Varicose veins are frequently treated by eliminating the insufficient veins. This forces the blood to flow through the remaining healthy veins. Various methods can be used to eliminate the problem of insufficient veins, including, sclerotherapy, surgery (vein stripping), electro-cautery, and laser treatments.

Sclerotherapy uses a fine needle to inject a solution directly into the vein. This solution irritates the lining of the vein, causing it to swell and the blood to clot. Specifically, the sclerosant acts upon the inner lining of the vein walls causing them to occlude and block blood flow. The vein turns into scar tissue that fades from view. Sclerotherapy may present numerous complications: allergic reactions, skin burns/damage and stains, blood clots and recurrence in large veins. Vein stripping procedure consists in stripping out problematic veins by passing a flexible device through the vein and removing it through an incision near the groin. Smaller tributaries of these veins are also stripped with this device or removed through a series of small incisions. Those veins that connect to the deeper veins are then tied off. Vein surgery results in scarring, bleeding and may occasionally cause traveling blood clots, nerve injury and swelling. Furthermore, procedures are long, require long recovery periods and are carried out under general, loco-regional or peridural anesthesia.

In radiofrequency (RF) treatment of insufficient veins, a RF catheter is positioned within the vein and the electrodes on the catheter are moved toward one side of the vein. RF energy is applied to cause selective heating of the vein and corresponding shrinkage of the adjacent venous tissue. This method has some disadvantages. RF energy in the treatment of vein insufficiency may be ineffective in certain cases and interventions can be lengthy and stressful for the patient.

Minimally invasive laser surgery has been improved due to new diode laser systems. For endovascular laser surgery, laser radiation applies thermal energy to the vein with the aid of an optical fiber, and while it is withdrawn, the vein closes and, ideally, eventually disappears through absorption. In these and other cases, endovascular laser treatment provides an effective technique for diminishing skin and vascular problems.

Prior art methods and devices are intended to treat insufficient veins by obliterating them. As a consequence, and in addition to their specific drawbacks mentioned previously, venous function is not restored in insufficient veins. Instead, these veins are either extracted or closed in order to prevent blood from circulating through them, thus avoiding reflux. The treated veins are no longer capable of conveying blood and generally are no longer present. As a consequence, vein is lost for future cardiac and other by-pass procedures. Furthermore, recurrence or persistence of varicose veins may occur, particularly if the valvular problem is not resolved. Summarizing, in these techniques vein function is destroyed, thus leading to consider them inappropriate to carry out procedures for restoring and preserving vein functionality.

An alternative, less invasive and more physiological approach focused on insufficient vein treatment would be to restore unidirectional blood flow back to the heart by recovering problematic vein functionality, instead of simply closing (or extracting) it in order to prevent any blood flow through it.

With the objective of carrying out vascular treatment by restoring venous function of insufficient veins, some approaches have been developed. These techniques are directed towards restoring venous function by making the valve competent.

Two main techniques for restoring venous functionality have been used: by means of implanting a venous valve; and by directly treating venous valvular incompetence.

In the first case, a valve is implanted inside the vein in order to replace insufficient valve. In general terms, implanted valve can be artificial (made from non-organic materials), a xenograft (from animals) or an autogenous graft (extracted from other site of patient's body). For instance, in U.S. Pat. No. 6,299,637, Shaolian et al. disclose a self expandable venous valve implant. It comprises a pivotable leaflet and a tubular wire support. Leaflet is positioned in the flow path, for permitting flow in a forward direction and resisting flow in a reverse direction.

In another example, disclosed by Gomez-Jorge et al. in WO00047136A1, a vascular valve prosthesis is formed by suturing a vein valve segment (for example, from a bovine jugular vein) which has been trimmed in order to reduce its thickness.

Venous valve implants present some disadvantages. Frequently, and especially in artificial prosthesis, implanted valves require an increased opening pressure. As a consequence, patient condition may further deteriorate, instead of improving. In addition, these surgical treatments require skillful and meticulous techniques, and often patients require multiple interventions. Furthermore, the use of compression stockings is often required even after surgical intervention to ensure relief of symptoms and durability of the operation. Moreover, implant rejection as well as thrombosis may occur in these procedures. Also procedure is more invasive, more time consuming and its outcome is not as predictable as vein obliteration. Therefore, cost-effectiveness becomes an important drawback.

In the second case, valve competence is intended to be restored by different means. For example, WO09638090A1 discloses an attempt to restore valve competence by reducing insufficient vein diameter. Vein lumen is constricted using an extravascular corrector attached to vein in the region of the incompetent valve. Corrector is made from a resilient shape-memory alloy in order to adapt to vein's structure. This technique presents some drawbacks. Since a foreign body is placed inside organism in this procedure, there are risks of infection and implant may be encapsulated or even rejected. In addition, material mechanical properties may be altered in time due to biological degradation. Furthermore, it is an invasive procedure.

In another approach, described in U.S. Pat. No. 6,322,559 by Daulton et al., vein diameter is also reduced just below an incompetent venous valve, by using a RF heating catheter that constricts the collagen layer. This catheter uses a low-voltage radiofrequency generator to heat expandable electrodes placed on catheter's tip (expandable coil). The surgical procedure consists in a percutaneous insertion of an introducer into the saphenous vein just below the level of the knee, under ultrasound guidance. The electrodes are then expanded to contact the vein wall and heated, during a treatment period of a few minutes. This approach presents some disadvantages. First, it is usually carried out under general or spinal anesthesia, with all associated risks and complications. Second, since the risk of thrombosis is believed to be substantial with this treatment, low-molecular weight (LMW) heparin is given subcutaneously before and after the procedure, during a week approximately, thus requiring professional attention over this time span. Third, it is a rather long procedure and recurrence is observed after one year, as vein is dilated almost to pre-treatment diameter. Finally, due to catheter's small diameter, it is only appropriate for small veins. If a larger catheter was used, greater veins could be treated, but size of catheter would make it too cumbersome to manipulate.

In order to restore venous function, the controlled shrinkage and strengthening of the vein structure needs to be accomplished. This in turn cannot be accomplished well and in a reliable manner by the relatively unspecific application of RF energy. RF treatment is limited to the reduction of vein diameter near the valve, hoping that consequently, valve will start working properly again, thus preventing reflux. However, if weakened valve is not treated and therefore still present, recurrence may occur.

In an alternative approach, U.S. Patent Publication 2006/0189967A1 by Masotti et al. describes a treatment of varicose veins by means of the recovery of the tone of the venous wall, using a pulsed holmium laser. This is disclosed to be accomplished by causing a hyalinizing sclerosis in the extracellular matrix of the median coat, but preserving tunica intima from thermal damage, using wavelengths between 800 and 2900 nm, preferably 2100 nm (holmium laser). This wavelength is proposed as it is characterized by a high absorption coefficient in water and a low absorption coefficient in hemoglobin. Nevertheless, experience has shown that wavelengths around this value are highly absorbed in blood (probably due to its high content of water), so it is unlikely that radiation would cause its major effect on the tunica media since absorption inside vein lumen will be high. In addition, pulsed holmium lasers usually emit radiation in narrow pulses. Thus, in order to achieve appropriate energy levels for producing certain effects on tissue, laser power should be high. High power radiation applied in short bursts may create undesired shockwaves, which in turn will produce undesired and unpredictable effects on tissue. It is well known by those skilled in the art that holmium lasers may not be recommendable for applications in which precise amounts of energy are to be applied and non-linear processes must be avoided. This patent also claims a wavelength range of 800-2900 nm, but effects produced in biological tissues due to the different wavelengths comprised in this range are substantially different. Therefore, it is unlikely that the desired described effect would be achieved with all the wavelengths in the claimed range. For instance, a wavelength of 800 nm is highly absorbed in hemoglobin, thus it is improbable that laser radiation reaches the tunica media without affecting tunica intima.

Size and cost are also important issues to take into account when using holmium lasers. Diode lasers, for example, have numerous advantages over ionic crystal lasers. Among them, it can be mentioned higher output, at reduced dimensions and weight. They also have simpler and smaller air cooling systems. Moreover, being integrated with optical fibers, they have a high reliability and do not need alignment.

As can be seen, effective and convenient treatment of venous valvular incompetence remains elusive.

Arteries, too, are affected by numerous pathologies. Among the most important are congenital anomalies and atherosclerosis.

Regarding congenital anomalies, aneurysms are among the most important. An aneurysm is an abnormal widening or ballooning of a portion of an artery due to congenital weakness in its wall. Aneurysms are most prominent and significant in the abdominal aortic artery, intracranial arteries (supplying blood to the brain), and the aorta, but also occur in peripheral vessels such as in the popliteal arteries, femoral arteries, carotid arteries, and in arteries feeding arms and kidneys. Although it is still not clear exactly what causes aneurysms, high blood pressure and high cholesterol may raise occurrence risk of certain types of aneurysms. The main complications of aneurysms include: compression of nearby structures such as nerves, infection and rupture, which can cause massive bleeding that may lead to death. Furthermore, thrombi may form in the dilated pouch, giving rise to emboli that may obstruct smaller vessels. In some cases, an aneurysm may dissect into the wall of an artery, blocking some of the branches.

Hypertension should be carefully controlled to prevent aneurysm formation or extension. Drugs are often prescribed to lower blood pressure and reduce the risk of rupture. Once an aneurysm forms, it will not disappear on its own. Medication may help slow down its growth, but does not represent a cure. Generally, most aneurysms eventually need repair.

Invasive treatments of aneurysms are either endovascular techniques (angioplasty with stent) or open surgery techniques. Open techniques include exclusion and excision. Exclusion of an aneurysm means tightly tying suture thread around the artery both proximally and distally to the aneurysm, to cut off blood flow through the aneurysm. If the aneurysm is infected or mycotic, it may then be excised. If uninfected, the aneurysm is often left in place. After exclusion or excision, a bypass graft can be placed, to ensure blood supply to the affected area.

For aneurysms in the aorta, arms, legs, or head, the weakened section of the vessel may be replaced by a bypass graft that is sutured at the vascular stumps. Instead of sewing, the graft tube ends, made rigid and expandable by nitinol wireframe, can be inserted into the vascular stumps and permanently fixed there by external ligature. Less invasive endovascular techniques allow covered metallic stent grafts to be inserted through the arteries of the leg and deployed across the aneurysm.

Endovascular treatments are less invasive and involve insertion of a catheter into the femoral artery in the patient's leg and navigating it through the vascular system, into the aneurysm. Tiny platinum coils are threaded through the catheter and deployed into the aneurysm, blocking blood flow into the aneurysm and preventing rupture. The coils are made of platinum so that they can be visible via X-ray and be flexible enough to conform to the aneurysm shape. Coil precipitates the formation of a thrombus within the aneurysm. The thrombus then partially or completely occludes the aneurysm. This way, blood from the parent vessel is prevented from flowing into and circulating within the aneurysm. Consequently, pressure on the weakened arterial wall at the aneurysm site is reduced as is the risk of rupture. This method has some disadvantages. There is a risk of coil migrating from the aneurysm to the parent artery and causing a thromboembolic stroke. Also, while the insertion of the coil and resulting thrombus could result in protecting the arterial wall at the aneurysm site, the method does not promote shrinkage of the aneurysm, nor address the expansion of the arterial wall at the aneurysm site.

Other prior art methods have been established for the exclusion of aneurysms, such as liquid embolics. The embolic material is injected in a liquid form through a small microcatheter into the affected area, where it begins to solidify, reducing the pressure and likelihood of rupture. However, here again, this tends to protect arterial wall and diminish probability of rupture but does not shrink the aneurysm or provide a cure for the expansion of the arterial wall at the aneurysm site.

An alternative approach is disclosed by Yamasaki et al. in U.S. Patent Publication 2008/0167637A1. Invention involves causing contractile force to be exerted on original aneurysm surface area so that original aneurysm surface area may contract and enclose volume smaller than original aneurysm volume. An irritant or polymer is dispensed to the inner surface area of an aneurysm to exert a contractile force on the inner surface area of the aneurysm, thereby shrinking the aneurysm. As a result, the artery wall at the aneurysm site is strengthened, the risk of rupture is decreased, and at least a partial cure for the expansion of the arterial wall at the aneurysm site is provided. This invention lacks efficiency since aneurysm shrinkage is achieved only partially. Furthermore, total effect is appreciated after several days, making it difficult for the surgeon to appropriately evaluate surgery results immediately after treatment.

In U.S. Patent Publication 2007/0129790A1, Peng discloses a treatment of aneurysms with an implantable polymeric, biodegradable device incorporating a matrix metalloproteinase (MMP) inhibitor. Treatment involves delivering polymeric, biodegradable implantable device incorporating drug comprising MMP inhibitor to the aneurismal site. This invention is directed towards small abdominal aortic aneurysms and its application is therefore limited. It also has the problems related generally to all implants.

As an alternative approach, thermal sources have been used for treating aneurysms. For instance, U.S. Pat. No. 4,735,201 by O'Reilly discloses an optical fiber with detachable metallic tip affixed to laser energy transmitting optical fiber by hot-melt adhesive. Metallic tip serves to generate heat by absorption of laser energy for cauterization of tissue surrounding the neck of an aneurysm or other vascular opening to be occluded. The device is used for intravascular laser coagulation of arteries, veins, aneurysms, vascular malformations and arteriovenous fistulas. The heat generating tip of the device is positioned intravascularly within the neck of the aneurysm or other vascular opening to be occluded and laser energy is transmitted through the optical fiber to heat the tip and thereby coagulate the tissue surrounding the tip.

As another example, U.S. Pat. No. 5,405,322, by Lennox, discloses an apparatus and method for treating an aneurysm in a vessel that isolates and evacuates volume around aneurysm site by application of RF heating, via spaced electrodes and one or more inflatable balloons within catheter. An apparatus and method for treating an aneurysm in a vessel that isolates a volume around the aneurysm, evacuates that volume and heats the aneurismal wall. A catheter includes one or more inflatable balloons for defining the isolated volume and occluding and preventing any blood flow through the volume. Suction applied through the catheter to the isolated volume withdraws any blood in the isolated volume and displaces the tissue for contact with a thermal source that heats the aneurismal wall. When the treatment is completed, the balloons are deflated and the catheter is removed from the vessel. Thermal sources present many disadvantages. First, as heat is an unspecific source of energy, treatment precision may be compromised. Second, risk of thrombosis is believed to be substantial with this kind of treatments. Third, recurrence is likely to occur after some time. Finally, these thermal methods require maintained contact between heated tip and the vessel wall and thus deliver energy to the vein wall essentially only through such points of contact. Specifically, regarding to RF, some drawbacks can also be mentioned. RF methods can be more time consuming and thus more stressful to the patient than otherwise desired. Moreover, the catheters used here and RF electrodes are relatively complex and more expensive to manufacture than those developed for other methods. The need for evacuation of blood in the treatment site also complicates the system and method, providing additional aspects where failure can occur.

There is thus a need for a minimally invasive vascular treatment that improves on the state of the art, providing an accurate and precise vessel function restoration, to enhance safety and versatility, while reducing procedure time. The present invention addresses these needs.

OBJECTIVES AND BRIEF SUMMARY OF THE INVENTION

It is an objective of the present invention to provide a device and method for improved vascular treatment of vessel disorders.

It is also an objective of the present invention to provide a device and method for a safer, painless and more reliable vascular treatment to accomplish an effective vessel function restoration.

It is another objective of the present invention to treat dysfunctional vessels accurately and precisely, by using a localized, directed energy source and conveying means.

It is another objective of the present invention to reduce diameter of dilated vessels in a controlled manner.

It is yet another objective of the present invention to provide a radiation device and method of treating veins that preserves their structure and restores valve competence.

It is another objective of the present invention to provide a minimally invasive radiation device and method of treating life-threatening artery pathologies, such as aneurysms.

Briefly stated, a device and method for restoring functionality of blood vessels are disclosed. Laser energy is accurately and precisely applied in order to restore vessel functionality. This is accomplished by a controlled, reliable and specific shrinkage and/or strengthening of the vessel structure. Laser radiation is transported in a controlled manner via an optical fiber to the site where energy is needed. Laser wavelength is chosen according to the required penetration depth in tissue. It has been found that a wavelength that is essentially absorbed within less than a millimeter of the actual dimensions of the vessel walls thickness works best. In a preferred embodiment, wavelength of approximately 1470 nm is used. A mini-endoscope is preferably used to control the process by visual inspection from the inside of the vessel. Other means such as ultrasound, echography, Positron Emission Tomography (PET), Computed Tomography (CT) and Optical Coherence Tomography (OCT), or other imaging means can also be combined to control the procedure. Full 360° radial emission, i.e., delivery of laser radiation perpendicularly or fairly inclined relative to the veins axis, is beneficial, and is accomplished by means of a radial emitting fiber. In another preferred embodiment, a 360 degree radiation pattern can be achieved by using a twister or side-emitting fiber, along with rotational and sweeping movements, to apply energy in an even, more-controlled, and guided manner. Valve function is restored to recover whole vein functionality, avoiding the need of closing it. In a preferred embodiment, energy is applied from the outside of the vessel, by inserting a device through the skin and tissue. In another preferred embodiment, specific radiation absorbers (and/or scattering enhancers) can be located at suitable positions inside the vessel wall or near the tissue to be treated, thus radiation can then selectively target tagged locations. Vessel function is restored preserving its structure, using a minimally invasive treatment. A wide range of vessel diameters are effectively treated. Vessels include veins, arteries and fistulas. Specifically, when treating veins, valvular incompetence is accurately and precisely treated, thus rendering a safe, versatile and fast procedure with reduced recurrence possibilities.

The above and other objects, features and advantages of the present invention will become apparent from the following description read in conjunction with the to accompanying drawings (in which like reference numbers in different drawings designate the same elements).

DETAILED DESCRIPTION OF PREFERRED EMBODIMENTS

As previously mentioned, numerous approaches have been proposed for the treatment of vein and artery pathologies. However, these approaches present several drawbacks. Present invention discloses a device and method to restore venous function by controlled shrinkage and strengthening of the vein structure.

Figure 1:
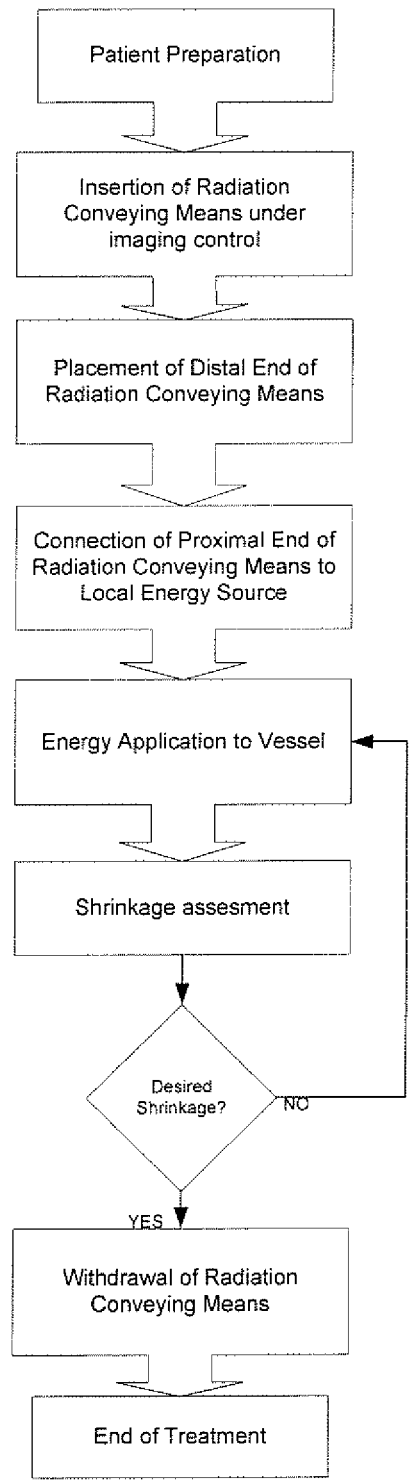
FIG. 1 depicts a preferred embodiment of present invention describing main steps of a general treatment.
Figure 2A:
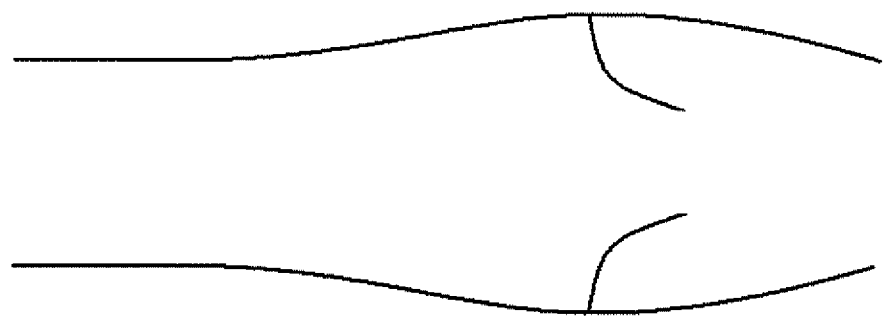
FIG. 2a depicts a sketch of a situation in which valve is incompetent due to vein dilation.
Figure 2B:
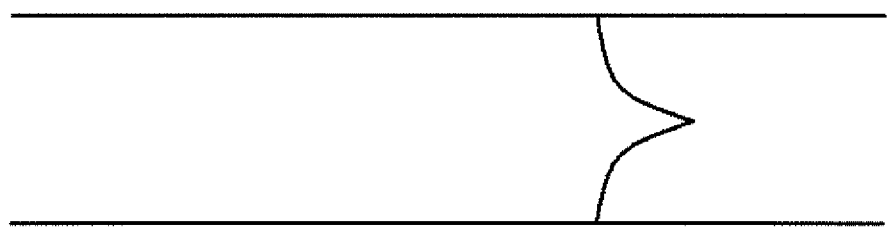
FIG. 2b depicts valve competence restoration as a consequence of vein diameter reduction.

In a preferred embodiment of present invention, a controlled, reliable and specific shrinkage of dilated vein near valves is accomplished. In FIG. 1, main steps of this embodiment are shown. In order to perform treatment, radiation is transported in a controlled manner via a radiation conveying means to the site where energy is needed. Radiation conveying means is inserted through the skin and inside the vein in order to perform an endoluminal procedure. In another preferred embodiment, energy is applied from the outside of the vein, by inserting the device through the skin and tissue. Once distal end of radiation conveying means is in the desired position, proximal end is connected to the energy emitting device and energy is applied to the vein wall. For instance, procedure could be carried out by applying a small amount of energy near all of the valves, then removing the catheter and checking functionality. If one or more valves still seem to close inadequately, procedure could be repeated by applying an additional small amount of energy. As a consequence of the energy absorbed in the vein, its diameter is reduced in a controlled manner, re-accomplishing the proper contact between the vein valve cusps and thus recovering venous function. FIG. 2a is a schematic drawing depicting a dilated vein in which it can be seen that valve cusps don't seal properly. After procedure is carried out, vein is shrunk and valve functionality is restored, as showed in FIG. 2b.

In some cases, valve structure can be weak or dysfunctional, thus proper closure may be compromised irrespective of vein diameter. As a consequence, vein shrinkage may not be sufficient for recovering vein functionality in these cases, since proper contact between vein valve cusps may not be achieved. In these cases, it may be necessary to irradiate valve itself in addition to vein wall, in order to strengthen its structure, due to collagen contraction. In another preferred embodiment, energy is applied in order to achieve two main effects: vein diameter reduction for getting valve cusps closer; and valve structure strengthening for accomplishing a proper seal between valve cusps. Restored valves could serve as a protection for the venous system by stopping the progression of the disease down the vein.

In a preferred embodiment, treatment methods disclosed are used to achieve a controlled, reliable and specific shrinkage of dilated vein and/or valve structure strengthening in vascular access veins. As previously mentioned, venous hypertension may occur in vascular access, thus causing valvular incompetence or central venous stenosis. When laser energy is applied to the vein structure, its absorption leads to diameter reduction in a controlled manner, re-accomplishing proper contact between the vein valve cusps and thus recovering venous function. Additionally, valves can be treated, rendering a stronger structure and improving treatment outcome.

In another preferred embodiment, the technique disclosed in the present invention is used for vein insufficiency prevention. In order to accomplish this objective, when performing a routine vein evaluation study at physician's office, dilated veins which are not yet insufficient (but show signs of becoming so in the near future) could be identified by means of an echographic study. At this point, symptoms do not yet represent an important physiological discomfort or an esthetic issue for the patient, although diagnostic information suggests that symptoms will be augmented in the near future, so a simple preventive treatment is recommendable. This preventive treatment may consist in irradiating dilated vein as previously explained, in order to reduce its diameter to normal or acceptable dimensions. As a consequence, vein function deterioration is slowed down or virtually eliminated. This preventive procedure could be repeated periodically (for example every two years) and would be a preferable choice, since by accepting it, patient would never get varicose veins symptoms, or these would be delayed in time.

Regarding artery pathologies, as mentioned earlier prior art treatments also present numerous drawbacks. Present invention discloses treating aneurysms in an efficient manner by means of the controlled shrinkage and strengthening of its wall structure.

In a preferred embodiment of the present invention, aneurysms are treated by applying direct laser energy of appropriate wavelength and pattern thus rendering shrinkage as well as strengthening of vessel wall. Treatment method is similar to that disclosed in FIG. 1, but for shrinking aneurysms in a controlled, reliable and specific manner. Radiation is transported in a controlled manner via a radiation conveying means to the site where energy is needed. Radiation conveying means is inserted through the skin and inside the artery to a location nearby aneurysm in order to perform an endoluminal procedure. In another preferred embodiment, energy is applied from the outside of the vessel, by inserting the device through the skin and tissue. Once distal end of radiation conveying means is in the desired position, proximal end is connected to the energy emitting device and energy is applied to the vein wall. As a consequence of the energy absorbed in the vessel wall, its diameter is reduced in a controlled manner, accomplishing the controlled shrinkage and strengthening of wall structure. This minimally invasive method of treating aneurysms can be used to prevent their growth at their early stages or to shrink larger ones.

In a preferred embodiment, a mini-endoscope is used to control the process by visual inspection from the inside of the vein. In addition, a real time imaging means such as ultrasound can be added to control the procedure. Alternative or additional imaging technologies may be used including but not limited to Positron Emission Tomography (PET), Computed Tomography (CT) or Optical Coherence Tomography (OCT).

When laser radiation is used to apply energy to the vessel, different wavelengths can be chosen. Laser wavelength is chosen, in the present case, according to the desired penetration depth in tissue. It has been found that a wavelength that is essentially absorbed within less than a millimeter fits best the actual dimensions of the vessel walls thickness. In a preferred embodiment, wavelength of approximately $1470\pm60$ nm is used. Radiofrequency and other energy supplies may be used to reliably and controllably perform the task and the method described, provided suitable enhancers and/or imaging means as described are used. Biological means such as growth factors or stimulants of collagen formation, for instance may be added to supplement and enhance the treatments effects by strengthening and speeding up the strengthening of the vessel structure.

In a preferred embodiment, radial emission, i.e., delivery of 360 degree laser radiation perpendicularly or fairly inclined relative to the veins axis, is advisable and useful, and can be accomplished by means of a radial-emitting fiber as described in US Patent Publication 2009/240242A1 by Neuberger. In another preferred embodiment, a 360 degree radiation pattern can be achieved by using a twister fiber (described in application Ser. No. 12/714,155 by Neuberger) or a side-emitting fiber, with rotational and sweeping movements, thus applying energy in an even, more controlled and guided manner. Within the scope of the invention, it is also possible to bring the output end(s) of energy delivery devices in contact or at a controlled distance from the tissue by means of spreaders, levers, balloons, spacers or other suitable means and it is possible to use fiber optic assemblies such as fiber optic bundles.

In yet another preferred embodiment, specific radiation absorbers (and/or scattering enhancers) can be located at suitable positions inside the vessel wall or near the tissue to be treated, thus radiation can then selectively target tagged locations. If scatterers or absorbers are used with suitable wavelengths, energy can be transported through thicker zones. If, for instance, the absorber works at a wavelength of 1064 nm, then such a wavelength can also be useful for treatment. Dye molecules could be suitable absorbers or scatterers.

Although the present invention has been disclosed for treating vessels in general, it is to be understood that it is not limited thereto and may be employed endoluminally or from the outside to treat hollow anatomical structures in other areas of the body which may be affected by similar pathologies.

Numerous advantages arise from using this invention. In the first place, this new vascular procedure restores vessel function preserving its structure and working on a minimally invasive basis. It is appropriate for effectively treating a wide range of vessel diameters. In addition, when treating vein insufficiency, valvular incompetence is accurately and precisely treated, rendering a safe, versatile and fast procedure with reduced recurrence possibilities. Finally, this invention can be used as a preventive procedure, making it a preferable choice. As a consequence, when treating veins as a prophylactic measure, patient would never suffer from serious varicose veins symptoms, or these would be delayed significantly in time.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method of restoring the function of blood vessels, comprising the steps of:
    positioning an optical fiber at a treatment site of a blood vessel;
    applying laser radiation having a wavelength of about 1470+60 nm via the optical fiber to a wall of the blood vessel near a valve structure at the treatment site;
    assessing whether a desired diameter reduction of the blood vessel at the treatment site has been achieved;
    assessing whether the valve structure at the treatment site has proper function by determining whether adequate valve closure occurs;
    if adequate closure of the valve structure at the treatment site has not been achieved, applying additional laser radiation directly to the valve structure to produce collagen contraction and strengthen the valve structure.

2. The method of claim 1., wherein the laser radiation is radially emitted from the optical fiber in a 360-degree radiation pattern.

3. The method according to claim 2, wherein a radial emitting fiber tip is used to apply said laser radiation to the treatment site of the blood vessel.

4. The method according to claim 2, wherein a side fiber is used to apply said laser radiation to the treatment site of the blood vessel.

5. The method according to claim 2 wherein a twister fiber is used to apply said laser radiation to the treatment site of the blood vessel.

6. The method according to claim 1, wherein the step of assessing whether a desired diameter reduction has been achieved includes visual inspection from inside the blood vessel with an endoscope.

7. The method according to claim 1, wherein the step of assessing whether a desired diameter reduction has been achieved employs a technique selected from the group consisting of ultrasound, echography, Positron Emission Tomography (PET), Computed Tomography (CT) and Optical Coherence Tomography (OCT).

8. The method according to claim 1, further including a step of inserting the optical fiber inside the blood vessel.

9. The method according to claim 1, further including a step of positioning a radiation absorber or scattering enhancer inside a wall of the blood vessel or near tissue at the treatment site of the blood vessel.

10. The method according to claim 9, wherein the radiation absorber or scattering enhancer is a dye molecule.

11. The method according to claim 1, further including a step of providing biological growth factors or biological stimulants of collagen formation at the treatment site of the blood vessel.

* * * * *